United States Patent [19]

Wales et al.

[11] Patent Number: 5,730,740

[45] Date of Patent: Mar. 24, 1998

[54] LATCH MECHANISM FOR SURGICAL INSTRUMENTS

[75] Inventors: Kenneth S. Wales, Mason; Charles A. Hansford; J. David Hughett, both of Hamilton, all of Ohio

[73] Assignee: Ethicon Endo-Surgery, Inc., Cincinnati, Ohio

[21] Appl. No.: 555,741

[22] Filed: Nov. 9, 1995

[51] Int. Cl.⁶ .................................................. A61B 17/00
[52] U.S. Cl. ................................................ 606/1; 606/205
[58] Field of Search .......................... 292/254; 606/206, 606/208, 1, 138–148; 81/318, 323

[56] References Cited

U.S. PATENT DOCUMENTS

| 1,881,250 | 10/1932 | Tomlinson. | |
|---|---|---|---|
| 4,003,380 | 1/1977 | Wien. | |
| 4,800,880 | 1/1989 | Catalano. | |
| 5,104,397 | 4/1992 | Vasconcelos et al. | 81/322 |
| 5,190,541 | 3/1993 | Abele et al. | 606/46 |
| 5,389,098 | 2/1995 | Tsuruta et al. | 606/41 |
| 5,409,478 | 4/1995 | Gerry et al. | 606/1 |
| 5,445,638 | 8/1995 | Rydell et al. | 606/51 |
| 5,458,598 | 10/1995 | Feinberg | 606/52 |

FOREIGN PATENT DOCUMENTS

| 0 392 547 A1 | 4/1989 | European Pat. Off. . |
| 0 392 548 A1 | 4/1989 | European Pat. Off. . |
| 0 565 049 A1 | 4/1992 | European Pat. Off. . |
| 44 00 409 A1 | of 0000 | Germany . |
| 0 418 761 A2 | 9/1989 | Germany . |

OTHER PUBLICATIONS

European Search Report.

Primary Examiner—Glenn K. Dawson
Attorney, Agent, or Firm—Bernard Shay

[57] ABSTRACT

A surgical instrument including a handle and a trigger is designed to be closed and latched by the operator, and includes a latch mechanism. The latch mechanism includes a latch on the grip, a latch knob including a latching notch on the trigger and a latch guide on the trigger to guide the latch hook into the latching notch.

22 Claims, 6 Drawing Sheets

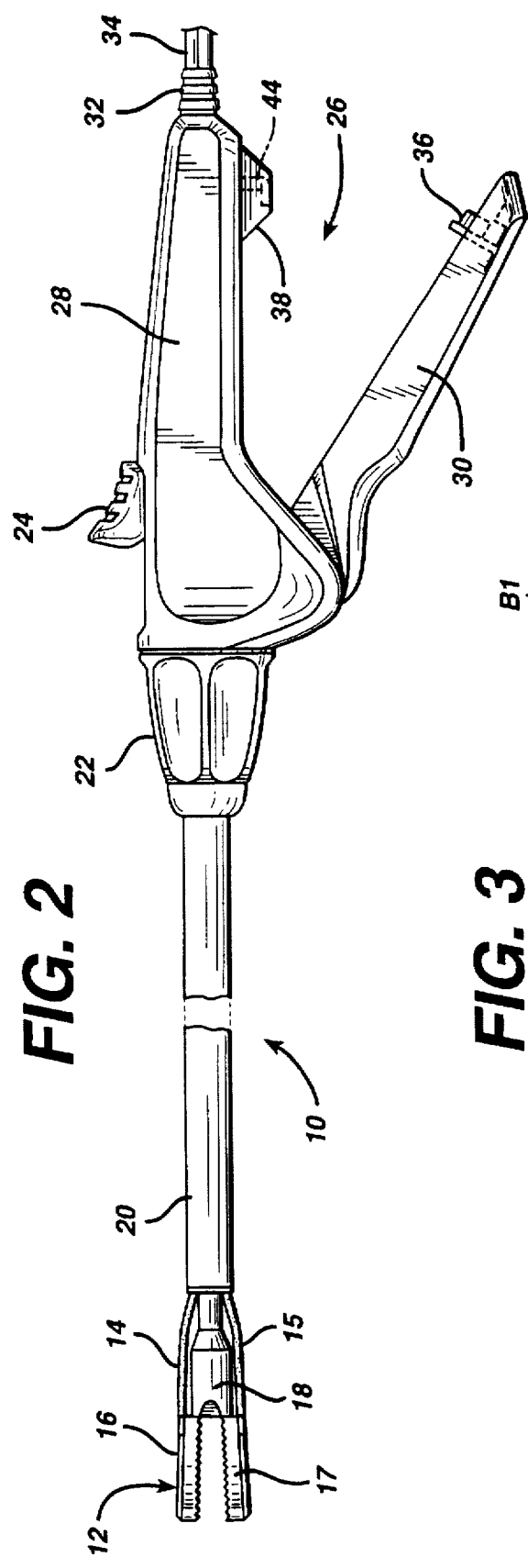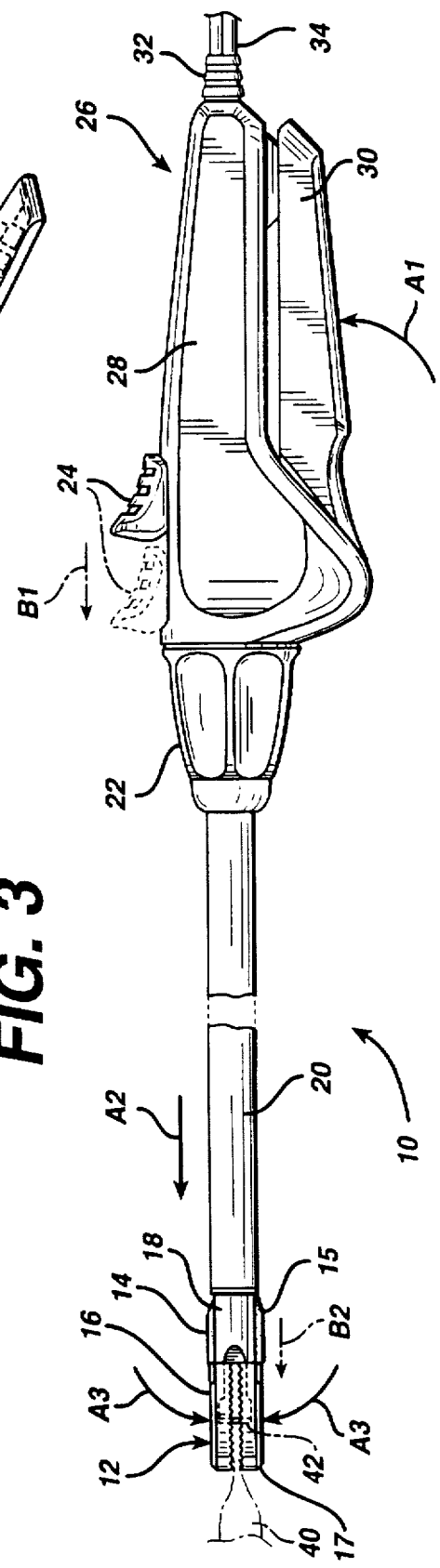
FIG. 2
FIG. 3

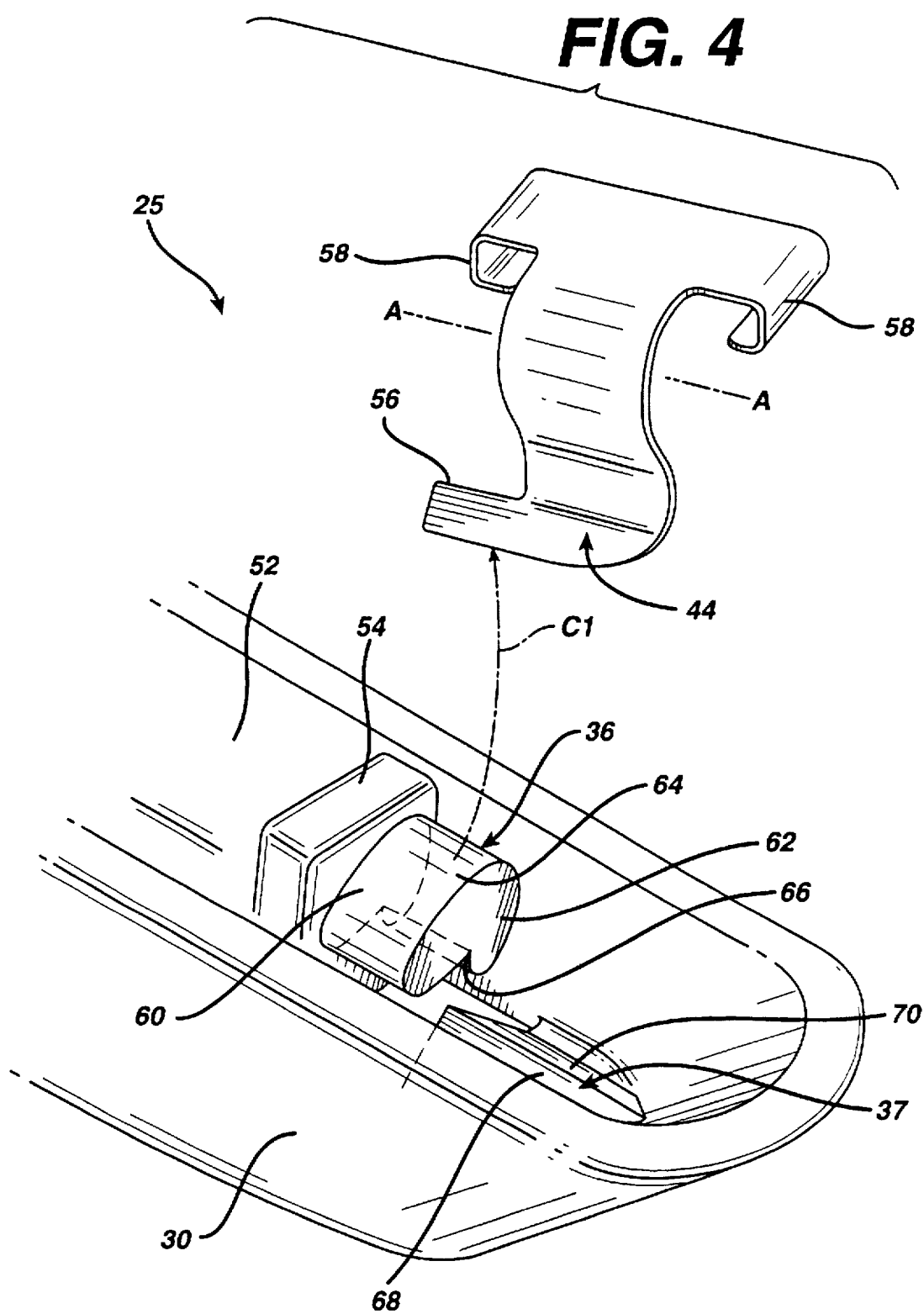

LATCH MECHANISM FOR SURGICAL INSTRUMENTS

This application is related to the following patent applications: application Ser. No. 08/537,065; application Ser. No. 08/536,726 now U.S. Pat. No. 5,679,220, and application Ser. No. 08/751,898.

The present invention relates, in general, to a latch mechanism and, more particularly, to an improved latch mechanism for use in surgical instruments.

BACKGROUND OF THE INVENTION

In many surgical instruments, end effectors are employed to, for example, grasp tissue. Such end effectors may be activated by moving a trigger mechanism or by closing a scissor type handle or, as in the surgical instrument illustrated in FIG. 1, by grasping a first member such as trigger 30 and pulling it toward a second member such as grip 28. In FIG. 1, pulling trigger 30 toward grip 28 acts to move closure tube 20 in a distal direction, closing jaws 16 and 17.

Once the end effector jaws have closed on the tissue, it may be advantageous to leave the jaws on the tissue for some period of time. For example, it may be necessary to leave the jaws closed in order to treat the tissue by applying electrical energy to the end effector. It may also be advantageous to manipulate tissue gripped by the end effectors. It would, therefore, be advantageous to use a latching mechanism on the trigger or handle to hold the end effector closed. In prior devices, a number of latching mechanisms have been used, including ratchet devices which allow the surgeon to adjust the pressure applied by the end effector. However, in some instruments, especially endoscopic instruments with small end effectors, it may be advantageous to utilize a single latch which is activated by closing the trigger and released by squeezing the trigger a second time. In addition, it may be advantageous to provide a latch for use on surgical instruments wherein an audible click indicates that the instrument is latched.

SUMMARY OF THE INVENTION

In a surgical instrument wherein two handle elements such as a handle and a trigger are designed to be closed and latched by the operator, the present invention relates to a latch mechanism which includes a latch on one handle element, for example, a grip, of the surgical instrument, a latch knob including a latching notch on a second handle element, for example, a trigger, and a latch guide positioned on the second handle element to guide the latch hook into the latching notch. According to the present invention, the latch knob is mounted on a mounting surface attached to the trigger and includes at least one deflecting surface adapted to deflect the latch in a first direction. Further according to the present invention the latch guide includes at least one guide surface adapted to guide the latch into the latch notch. Further, according to the present invention, the latch is adapted to flex around a fixed axis.

In operation a latch according to the present invention is deflected away from its center point by the deflecting surface as the trigger moves in the direction of the grip. Once the latch is released by the deflecting surface, it moves in a direction opposite the first direction until it encounters the guide surface. As the trigger is released, the latch moves along the guide until it encounters the notch. The latch is held in the notch by the spring force exerted on the trigger. When the spring force in the trigger is released by, for example, closing the trigger, the latch moves out of the notch and springs back to its centered position.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is a side elevational view of the surgical instrument illustrated in FIG. 1 shown in a first, unclamped position.

FIG. 3 is a side elevational view of the surgical instrument illustrated in FIG. 1 shown in a second, clamped position.

FIG. 4 is an enlarged perspective view of a latch mechanism according to the present invention.

DETAILED DESCRIPTION OF THE INVENTION

Figure 1:
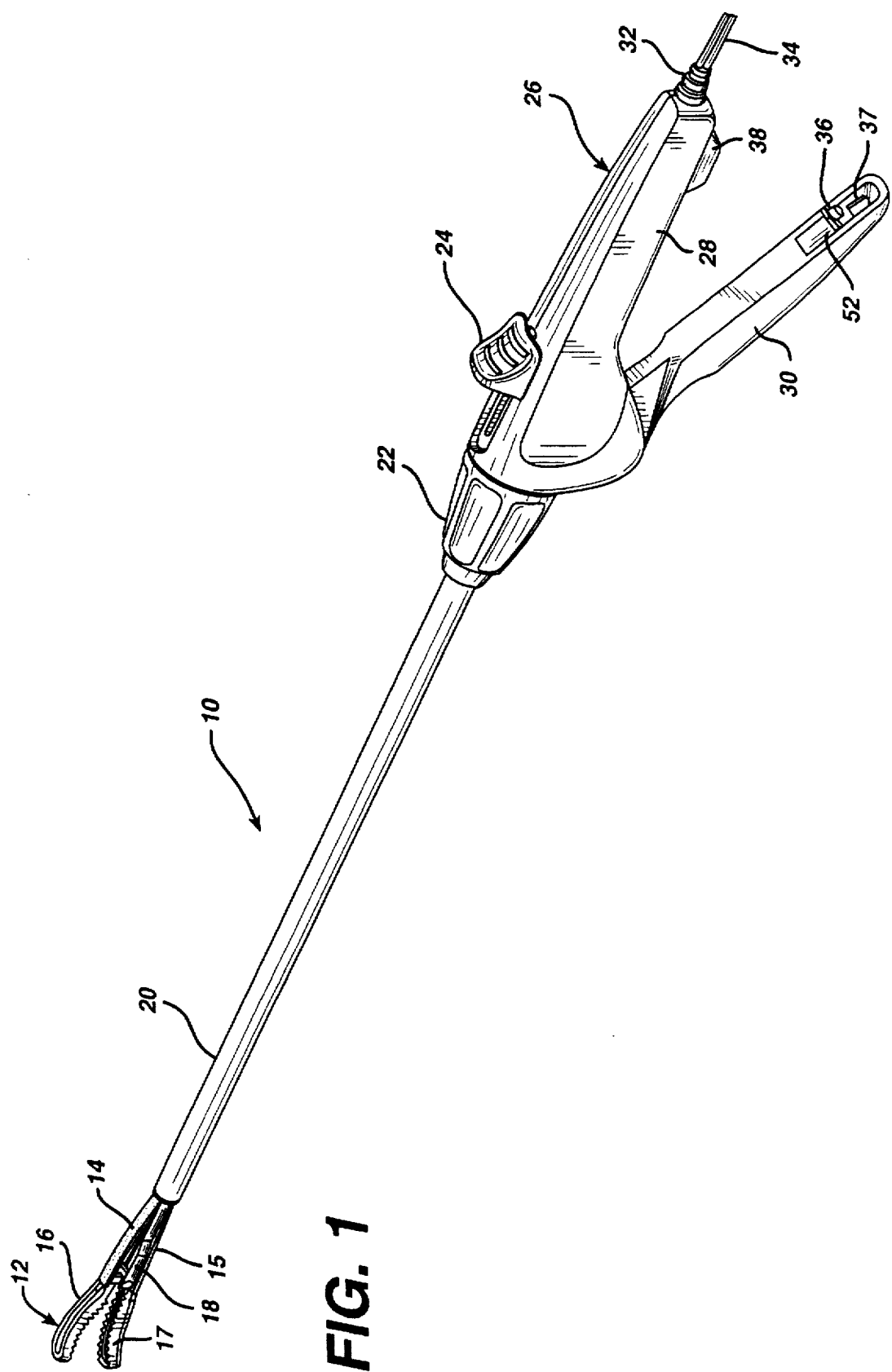
FIG. 1 is a perspective view of a surgical instrument including a latch mechanism according to the present invention.

FIG. 1 is a perspective view of a surgical instrument 10 which may be, for example, a bipolar cutting and coagulating instrument. The device illustrated in FIG. 1 includes a latching mechanism according to the present invention. In surgical instrument 10, upper jaw 16 and lower jaw 17 of end effector 12 are supported by upper wireform 14 and lower wireform 15, respectively. Wireforms 14 and 15 also act as conductors, supplying bipolar electrical energy to upper jaw 16 and lower jaw 17, respectively. Tissue stop 18 is positioned within closure tube 20. Rotation knob 22 is affixed to closure tube 20 to cause rotation of closure tube 20 with respect to handle 26. Handle 26 includes knife button 24, grip 28 and trigger 30. Electrical cord 34 is connected to handle 26 through strain relief 32. Latch knob 36 and latch guide 37 are positioned on trigger 30. Handle latch shield 38 is positioned on grip 28.

FIG. 2 is a side elevational view of the surgical instrument illustrated in FIG. 1 shown with trigger 30 open. FIG. 3 is a side elevational view of the surgical instrument illustrated in FIG. 1 shown with trigger 30 closed and latched. As illustrated in FIGS. 2 and 3, bipolar forceps 10 have a first open position and a second, closed position. In the open position, illustrated in FIG.. 2, trigger 30 is biased open by a spring or other mechanism, allowing closure tube 20 to move to its proximal position. With closure tube 20 in its proximal position the spring force in wireforms 14 and 15 separate jaws 16 and 17 of the end effector 12. In FIG. 2, latch 44 is illustrated in outline form inside of handle latch shield 38.

As illustrated in FIG. 3, movement of trigger 30 in direction A1, towards grip 28, forces closure tube 20 to move in direction A2, away from handle 26. As closure tube 20 moves in a distal direction, closure tube 20 forces wireforms 14 and 15 towards tissue stop 18. Wireforms 14 and 15, in turn, force jaws 16 and 17 to move in direction A3. When tissue 40 is positioned between jaws 16 and 17 of end effector 12, closing trigger 30 causes jaws 16 and 17 to close and grip the tissue. Jaws 16 and 17 hold the tissue while it is being treated by, for example, applying high frequency bipolar energy. Alternatively, or after treatment of the tissue, a knife 42 may be advanced into end effector 12. As illustrated in FIG. 3, knife 42 advances in direction B2 when knife button 24 is advanced in direction B1. Tissue stop 18 acts to shield knife 42 when knife 42 is in its retracted or proximal position.

FIG. 4 is an enlarged, perspective view of a latch mechanism 25 according to the present invention. In FIG. 4, latch 44 is shown without grip 28 and latch shield 38 for clarity. Tabs 58 are used to mount latch 44 to grip 28. Latch 44 is adapted to bend or flex along an axis which is substantially parallel to line A—A. Latch 44 is preferably constructed of a spring material such as metal. Thus, deflection of latch 44 results in an opposing spring force which acts to move latch 44 back toward its original or centered position. Latch hook 56 protrudes from latch 44 in a direction substantially parallel to line A—A. Latch hook 56 is positioned at a distance from grip 28 to enable it to engage latch knob 36 when trigger 30 is closed. The embodiment of latching mechanism 25 illustrated in FIG. 4 includes an S-shaped latch 44 which may be particularly well adapted for the embodiment of the invention illustrated in FIG. 4. In particular, the S-shape of latch 44 results in latch hook 56 being oriented along the surface of latch knob 36, thus facilitating movement of latch hook 56 along the surface of latch knob 36 and preventing the latch hook from catching on the back side of latch knob 36.

In the embodiment of the invention illustrated in FIG. 4, trigger 30 includes a recess 52. Recess 52 includes latch knob 36, latch guide 37 and mounting wall 54. In the embodiment illustrated in FIG. 4, latch knob 36 includes a first end 60 which is affixed to mounting wall 54, a second end 62 opposite first end 60, a guide surface 64 and a latching notch 66. In the embodiment of the invention illustrated in FIG. 4, latch guide 37 is positioned in recess 52, below latch knob 36. At least a portion of latch knob 36 is positioned distal of latch guide 37. Latch guide 37 includes at least a first guide surface 68 and may also include a second guide surface 70.

Figure 5A:
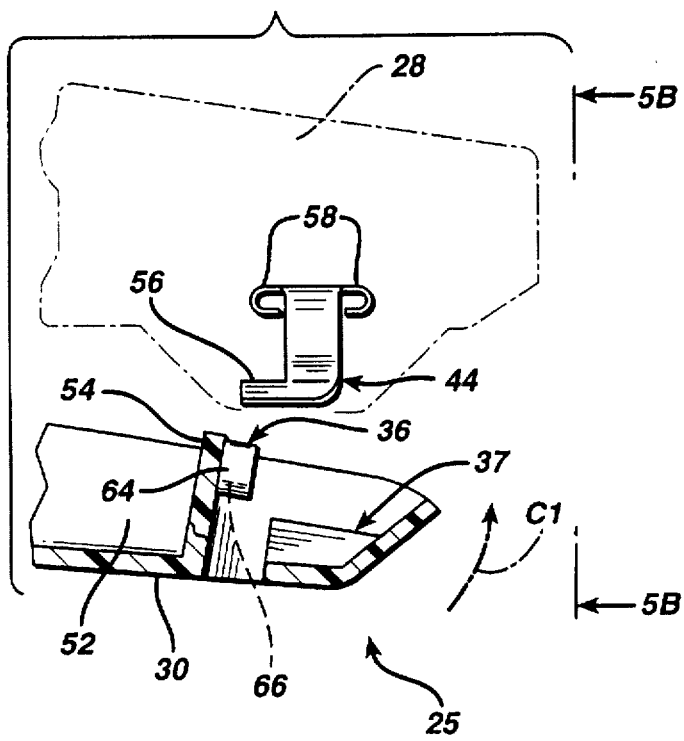
FIGS. 5A, 6A, 7A and 8A are fragmentary side views of the latching mechanism illustrating the relationship of the various elements during the closing and opening of the instrument.
Figure 5B:
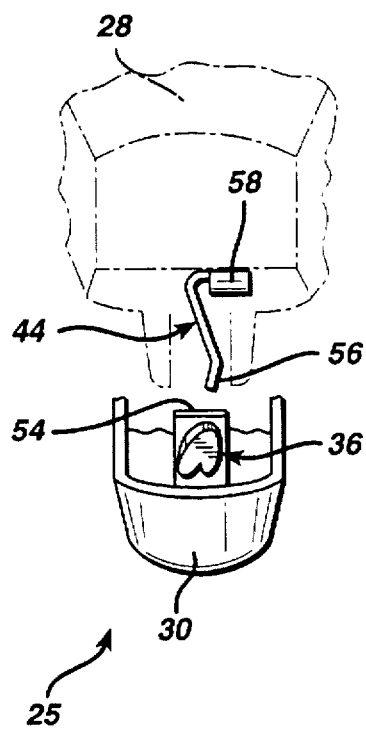
FIG. 5B is an end view of the latch mechanism in a first, open position as seen along view line 5B—5B of FIG. 5A.
Figure 6A:
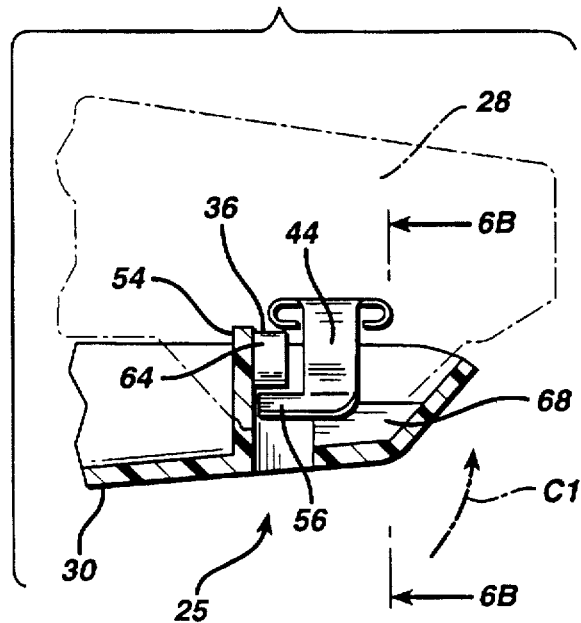
Figure 6B:
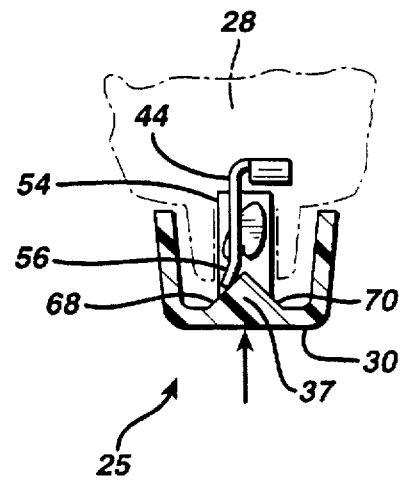
FIG. 6B is a cross-sectional view of the latch mechanism in a second, position as seen along section line 6B—6B of FIG. 6A.

FIGS. 5A,B through 8A,B illustrate a motion diagram for latch mechanism 25. In this diagram the motion sequence is: a). Fully close trigger 30 as illustrated in FIGS. 5 and 6; b) Release trigger 30, causing the mechanism to latch as illustrated in FIG. 7; c) Reclosing trigger 30, causing the mechanism to unlatch and allowing the trigger to open as illustrated in FIG. 8. As trigger 30 closes, ramped surface 64 deflects springy latch 44 to the side. When trigger 30 bottoms out latch hook 56 is spring loaded and ready to travel into latch notch 66. Releasing trigger 30 causes latch hook 56 to engage the latch notch 66. Squeezing trigger 30 allows latch 44 to deflect to the right, releasing latch hook 56. Releasing the trigger allows it to open along with the jaws.

More particularly, FIGS. 5A,B through 8A,B are views of latching mechanism 25 according to the present invention wherein the operation of latching mechanism 25 is illustrated. As illustrated in FIGS. 5A and B, the operation of latch mechanism 25 according to the present invention is initiated by the operator closing trigger 30 by pulling trigger 30 toward grip 28 along path C1. As trigger 30 nears the end of its close stroke, latch 44 touches latch knob 36 and is forced in a first direction by guide surface 64 of latch knob 36. As illustrated in FIG. 6A and B, upon further movement of trigger 30 in direction C1, latch hook 56 moves past guide surface 64 and snaps against first guide surface 68 of Latch guide 37 with an audible "click". Latch 44 is held against first surface 68 of latch guide 37 for so long as the operator maintains pressure in direction C1.

Figure 7A:
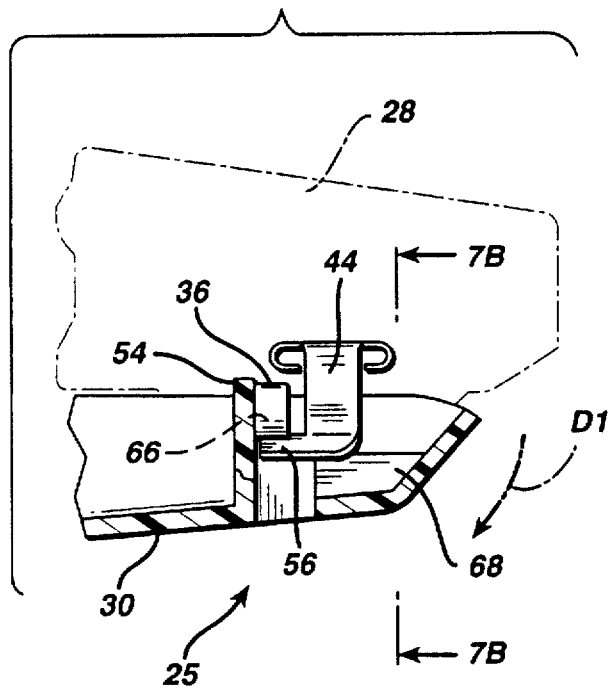
Figure 7B:
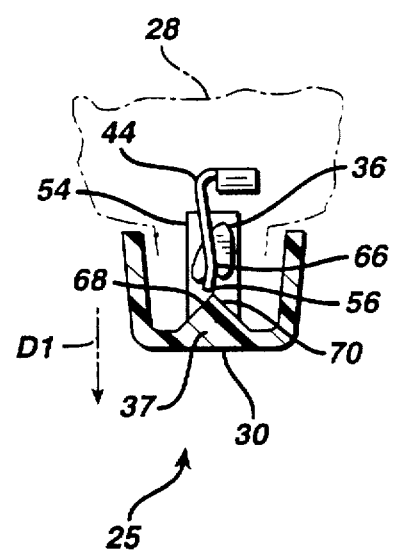
FIG. 7B is a cross-sectional view of the latch mechanism in a third, latched position as seen along section line 7B—7B of FIG. 7A.

As illustrated in FIG. 7A and B, when the operator releases pressure on trigger 30, the spring forces act to move trigger 30 in direction D1. As trigger 30 moves in direction D1, latch 44 moves along surface 68, towards latching knob 36. When latch 44 reaches the end of surface 68, the spring forces in latch 44 move latch 44 past latch guide 37 and move latch hook 56 into latch notch 66. The combined spring forces on latch 44 and trigger 30 act to hold latch hook into latch notch 66 until counter pressure is applied to latch trigger 30 to force latch hook 56 out of latch notch 66. Thus, with latch hook 56 in latch notch 66, latching trigger 30 is latched in the closed position.

Figure 8A:
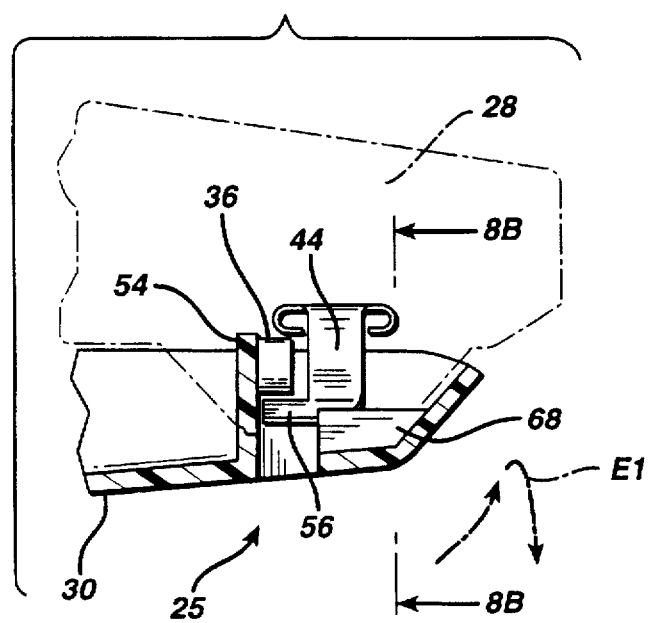
Figure 8B:
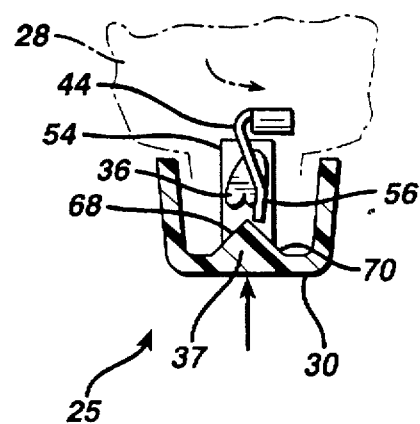
FIG. 8B is a cross-sectional view of the latch mechanism in a fourth, unlatched position as seen along section line 8B—8B of FIG. 8A.

As illustrated in FIG. 8A and B, trigger 30 is released by moving trigger 30 toward grip 28 and then releasing the pressure on trigger 30. Thus, trigger 30 is released by moving trigger 30 along path E1 in FIG. 8A. More particularly, to release trigger 30, pressure is applied on trigger 30 which forces latch hook 56 down and out of latching notch 66. Guide surface 70 works with the residual spring tension on latch 44 to move latch hook 56 out past latch knob 36 to its central position so that when trigger 30 is released, latch 44 is released, allowing trigger 30 to move away from grip 28.

Figure 9:
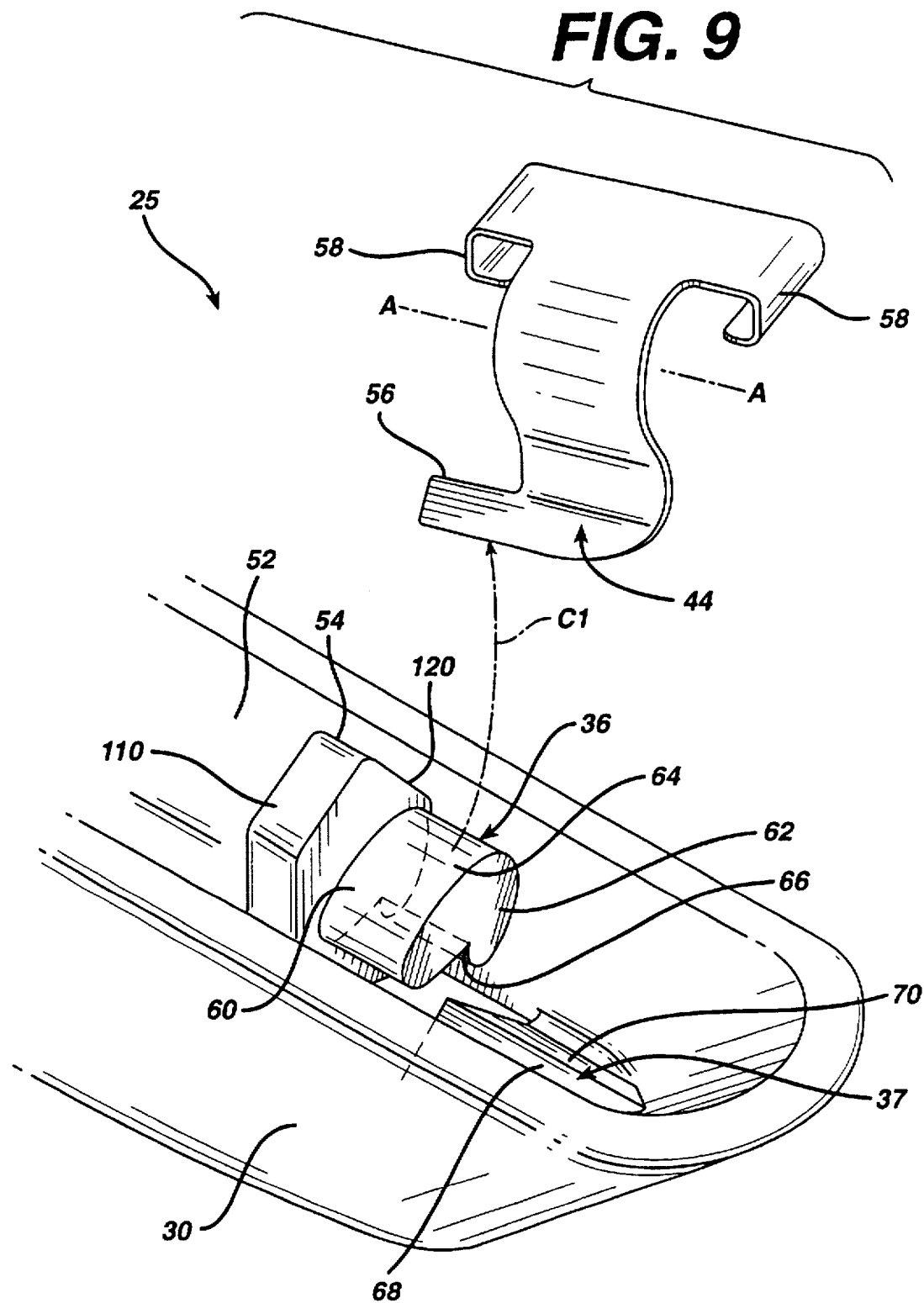
FIG. 9 is an enlarged perspective view of a latch mechanism according to the present invention.

As illustrated in FIG. 9, an orientation guide 100 may be included on, for example, trigger 30 to ensure that latch 44 is properly aligned with latch knob 36 as trigger 30 is closed. Although many orientation guides would be suitable for aligning the latch described, the orientation guide in FIG. 9 includes a pair of surfaces 110 and 120 which are located on mounting wall 54 and are adapted to interact with latch shield 38 to position latch 44 opposite guide surface 64 of latching knob 36. Thus, as trigger 30 is closed, the walls of latch shield 38 move along surfaces 110 or 120 and latch 44 is centered above surface 64.

This latching mechanism is particularly suitable for devices such as electrocautery devices where the surgeon may need to keep the jaws closed on tissue as RF energy is applied. The addition of an auditory sound to the latch also enhances the latch. This mechanism can also be utilized on other open and endoscopic surgical devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument including a latch mechanism, said latch mechanism comprising:
   a latch attached to and extending from a first handle of said surgical instrument;
   a latch knob including a guide surface and a latching notch on a second handle of said surgical instrument; and a latch guide on said second handle of said surgical instrument.

2. A surgical instrument according to claim 1 wherein said latch comprises a flexible body and a latch hook.

3. A surgical instrument according to claim 2 wherein said latch hook is located at an end of said flexible body opposite said first handle.

4. A surgical instrument according to claim 1 wherein said guide surface is positioned to contact said latch as said first handle is brought together with said second handle and is adapted to guide at least a portion of said latch into said latching notch.

5. A surgical instrument according to claim 4 wherein said latch comprises a flexible body and a latch hook, said latching notch being oriented substantially parallel to said latch hook.

6. A surgical instrument according to claim 1 wherein:

said latch comprises a flexible body adapted to move in first and second directions and a latch hook;

said guide surface is positioned to contact said latch and move said latch in said first direction as said first handle is brought together with said second handle;

said latch guide is positioned to limit the movement of said latch in said second direction as said latch moves past said guide surface.

7. A surgical instrument according to claim 6 wherein said latch guide is positioned to guide said latch hook into said latch notch as said first and said second handles move away from each other.

8. A surgical instrument including a latch mechanism, said latch mechanism comprising:

a latch attached to and extending from a first handle of said surgical instrument, wherein said latch comprises:
a flexible latch body adapted to flex around an axis; and
a latch hook extending from said latch body in a direction substantially parallel to said axis;

a latch guide on a second handle of said surgical instrument, wherein said latch guide comprises a first surface, said first surface being sloped toward a latching notch; and a latch knob on a mounting surface attached to said second handle of said surgical instrument, wherein said latch knob comprises:
at least one deflecting surface; and
said latching notch.

9. A surgical instrument according to claim 8 wherein said deflecting surface is adapted to move said latch hook in a first direction substantially perpendicular to said axis and said latching notch is arranged substantially parallel to said axis.

10. A surgical instrument according to claim 9 wherein said latch has a spring force such that movement of said latch in said first direction is opposed by said spring force.

11. A surgical instrument according to claim 10 wherein said latch guide is positioned to oppose movement of said latch in a second direction.

12. A surgical instrument according to claim 11 wherein said deflecting surface moves said latch a first distance in said first direction and said latching notch is located between said first distance and a resting position of said latch.

13. A surgical instrument including first and second elongated handles and including a latch mechanism, said latch mechanism comprising:

a latch hook connected to and spaced from said first handle such that said latch hook is adapted to move in a first direction and in a second, opposite direction;

a latch knob including a latching notch connected to a mounting surface of said second handle, said latch knob extending from said mounting surface in a direction which is substantially perpendicular to said first direction;

a latch guide extending from said second handle and having at least a first surface separated from said latching notch;

said first elongated handle includes first and second walls on either side of said latch hook; and said second elongated handle including an orientation guide.

14. A surgical instrument according to claim 13 wherein said orientation guide comprises a first sloped surface and a second sloped surface.

15. An endoscopic surgical instrument comprising:

a handle wherein said handle comprises a first handle element and a second handle element and a knife trigger;

an end effector connected to said handle through an elongated tube, wherein said end effector comprises:
a pair of grasping jaws; and
a knife adapted to move between said jaws wherein said knife is connected to said knife trigger; and a latch mechanism, said latch mechanism comprising:
a latch attached to and extending from said first handle of said surgical instrument; and
a latch knob including a guide surface and a latching notch on said second handle of said surgical instrument.

16. An endoscopic surgical instrument according to claim 15 wherein said latch comprises a flexible body and a latch hook.

17. An endoscopic surgical instrument according to claim 16 wherein said latch hook is located at an end of said flexible body opposite said first handle.

18. An endoscopic surgical instrument according to claim 15 wherein said guide surface is positioned to contact said latch as said first handle is brought together with said second handle and is adapted to guide at least a portion of said latch into said latching notch.

19. An endoscopic surgical instrument according to claim 18 wherein said latch comprises a flexible body and a latch hook, said latching notch being oriented substantially parallel to said latch hook.

20. An endoscopic surgical instrument according to claim 15 further comprising a latch guide on said second handle of said surgical instrument.

21. An endoscopic surgical instrument according to claim 20 wherein:

said latch comprises a flexible body adapted to move in first and second directions and a latch hook;

said guide surface is positioned to contact said latch and move said latch in said first direction as said first handle is brought together with said second handle;

said latch guide is positioned to limit the movement of said latch in said second direction as said latch moves past said guide surface.

22. An endoscopic surgical instrument according to claim 21 wherein said latch guide is positioned to guide said latch hook into said latch notch as said first and said second handles move away from each other.

* * * * *